US008977368B2

(12) United States Patent
Doerr et al.

(10) Patent No.: US 8,977,368 B2
(45) Date of Patent: Mar. 10, 2015

(54) IMPLANTABLE DEVICE

(75) Inventors: Thomas Doerr, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 685 days.

(21) Appl. No.: 13/301,632

(22) Filed: Nov. 21, 2011

(65) Prior Publication Data

US 2012/0157809 A1  Jun. 21, 2012

Related U.S. Application Data

(60) Provisional application No. 61/424,071, filed on Dec. 17, 2010.

(51) Int. Cl.
*A61N 1/08* (2006.01)
*A61B 5/04* (2006.01)
*A61N 1/05* (2006.01)

(52) U.S. Cl.
CPC *A61N 1/056* (2013.01); *A61N 1/08* (2013.01); *A61N 2001/086* (2013.01)
USPC ............ 607/119; 607/122; 607/123; 600/374

(58) Field of Classification Search
CPC ... A61N 1/056; A61N 1/08; A61N 2001/086; A61N 18/1492
USPC ............................ 600/374; 607/119, 122, 123
See application file for complete search history.

(56) References Cited

U.S. PATENT DOCUMENTS

| | | | |
|---|---|---|---|
| 5,766,153 A * | 6/1998 | Eggers et al. | 604/114 |
| 8,386,057 B2 * | 2/2013 | Flach et al. | 607/119 |
| 2004/0199071 A1 | 10/2004 | Lardo et al. | |
| 2007/0288058 A1 | 12/2007 | Halperin et al. | |
| 2009/0281592 A1 | 11/2009 | Vase | |
| 2009/0306738 A1 * | 12/2009 | Weiss et al. | 607/30 |
| 2010/0016936 A1 | 1/2010 | Stevenson et al. | |

OTHER PUBLICATIONS

European Search Report dated Feb. 20, 2012 (7 pages).

* cited by examiner

*Primary Examiner* — Tammie K Heller
(74) *Attorney, Agent, or Firm* — ARC IP Law, PC; Joseph J. Mayo

(57) ABSTRACT

An implantable medical device having at least one first and one second longitudinally extended electrical functional conductor to transmit therapeutic signals or diagnostic signals or both. The implantable medical device includes one electrode pole connected to the functional conductor, wherein electrical current is delivered to the surrounded bodily tissue using the electrode pole. Electrical potentials may be sensed in the surrounding tissue using the electrode pole, such that the two electrical functional conductors are inductively coupled for defined resonant frequencies and such that RF energy of a first functional conductor is diverted to the second functional conductor. The RF energy is delivered to the surrounding tissue via the second functional conductor and via an electrode pole connected to the second functional conductor.

6 Claims, 9 Drawing Sheets

IMPLANTABLE DEVICE

This application claims the benefit of U.S. Provisional Patent Application 61/424,071 filed on 17 Dec. 2010, the specification of which is hereby incorporated herein by reference.

BACKGROUND OF THE INVENTION

1. Field of the Invention

Embodiments of the invention relate to a permanently or temporarily implantable device having a longitudinally extended electrical conductor.

2. Description of the Related Art

Such devices, for example, electrode conductors for electrical stimulation or catheters with electrodes, have the disadvantage that the electrical leads thereof can heat up in an MRI machine because the alternating magnetic fields in an MRI machine induce electrical currents in the electrical conductor which are not insignificant. For this reason, patients with heart pacemakers usually cannot be examined in an MRI machine using today's technology or can be examined only to a limited extent.

Implantable heart pacemakers or defibrillators typically have at least one stimulation electrode lead attached to said pacemaker, wherein said electrode lead has a standardized electrical connection at its proximal end, said end being provided for connection to the heart pacemaker or defibrillator and said electrode lead having one or more electrode poles on its distal end, said distal end being provided for locating the same in the heart. Such an electrode pole serves to deliver electrical pulses to the (myocardial) tissue of the heart or to sense electrical fields, in order to be able to sense an activity of the heart as part of so-called sensing. To this end, electrode poles typically form electrically conductive surface sections of an electrode lead. Electrode poles are typically provided as ring electrodes in the form of a ring around the electrode lead or in the form of a point or tip electrode at the distal end of the electrode lead. The electrode poles are electrically connected to contacts of the electrical connection of the electrode lead at its proximal end via one or more electrical conductors. Thus, one or more electrical conductors run between the contacts of the electrical connection of the electrode leads at their proximal end and the electrode poles at the distal end of the electrode lead, electrically connecting one or more of the electrode poles to one or more of the contacts. These electrical conductors may in turn be used for transmitting stimulation pulses to the electrode poles and to transmit electrical signals picked up by the electrode poles to the proximal end of the electrode lead and are also referred to as functional leads in the course of the further description. Such functional leads are electrical conductors, which are necessary for the function of the respective electrode lead and as such are exposed to the risk that electrical currents are induced in them due to external alternating magnetic fields. This electrical current may, for instance, result in unwanted heating of the functional leads or of the electrode poles connected to them or may result in a discharge of corresponding currents via the electrode poles into the surrounding tissue, thereby heating the surrounding tissue.

BRIEF SUMMARY OF THE INVENTION

The problem addressed by one or more embodiments of the invention is that of creating a device, which solves the problem described above.

According to one or more embodiments of the invention, this problem is solved by a device having at least two longitudinally extended electrical functional conductors for transmitting therapeutic signals or diagnostic signals or both, and having an electrode pole connected to one of the functional conductors, by which electrical current is delivered to the surrounding bodily tissue in the case of use or with which electrical potentials in the surrounding tissue can be sensed in the event of use, or both. The two electrical functional conductors are inductively coupled for defined resonant frequencies, so that RF energy of a first functional conductor is diverted to a second functional conductor, and the energy is delivered via this functional conductor and an electrode pole connected to this functional conductor to surrounding tissue in the event of use. It is possible in this way to divert RF energy induced in the event of use to an electrode pole suitable for distributing this energy.

According to a preferred embodiment variant, the medical device is a bipolar or multipolar catheter for temporary use or a permanently implantable electrode lead or some other longitudinally extended, electrically conductive implant having partial insulation, so that local heating due to MRI-induced currents is to be expected on defined electrode surfaces, such that the RF energy of a first lead, as the first functional conductor, is diverted by means of an inductive coupling for defined resonant frequencies, i.e., it is diverted to a second or additional lead as the respective second functional conductor, which then delivers the energy to the surrounding tissue via an electrode pole.

The electrode pole, which is connected to the respective second functional conductor, is preferably formed by at least one ring electrode. This ring electrode may be a functional ring electrode, which also serves to deliver stimulation pulses or to detect potentials. Alternatively, the ring electrode may also be provided only for diverting induced energy, that is, it may not have any other function, so that it is also referred to below as being nonfunctional. In the latter sense, a preferred embodiment variant is one in which the second functional conductor is electrically connected to at least one additional ring electrode as an electrode pole, which is provided specifically for diverting induced RF energy.

The medical device is preferably a stimulation electrode lead for connection to a permanently implantable stimulator, for example, a heart pacemaker or defibrillator, to enable the users of such implants to be examined in an MRI machine.

For inductive coupling of the two functional conductors, a transformer is preferably connected between the first and second functional conductors. In addition, a capacitor connected in parallel or in series with a winding of the transformer is preferably provided for tuning the resonant frequency of the inductive coupling circuit, comprised of a transformer and a capacitor. The capacitor is preferably connected to the secondary winding of the transformer, which is in turn connected to the second functional conductor.

The transformer and a capacitor, which is optionally present, are preferably tuned to one another in such a way that a desired resonant frequency is obtained, taking into account a parasitic capacitance to be expected in the event of use, to the surrounding body tissue and surrounding body fluid.

It is especially preferred if the transformer has no core. Alternatively, the transformer may have a core of ferromagnetic core material. In this case, the core preferably utilizes a ferromagnetic core material, whose saturation begins only at an MRI magnetic field strength higher than that expected.

In addition to the embodiments described herein other alternative embodiments may include some or all of the disclosed features.

BRIEF DESCRIPTION OF THE DRAWINGS

Embodiments of the invention will now be explained in greater detail on the basis of embodiments with reference to the figures. The figures show the following.

DETAILED DESCRIPTION OF THE INVENTION

The implantable heart stimulator 10 may be a heart pacemaker or a cardioverter/defibrillator (ICD). In the embodiment shown here, the heart stimulator 10 is a ventricular heart pacemaker and defibrillator. Other known heart stimulators are two-chamber heart pacemakers for stimulation of the right atrium and the right ventricle or biventricular heart pacemakers, which are additionally able to stimulate the right ventricle as well as the left ventricle.

Such stimulators typically have a housing 12, which is usually made of metal and is therefore electrically conductive and may serve as a large-surface-area electrode pole. Typically a terminal housing 14 is attached to the outside of the housing 12 and is also referred to as a header. Such a header typically has female contacts to receive plug contacts. The female contacts have electrical contacts 16, which are connected via corresponding conductors to electronics provided in the housing 12 of the heart stimulator 10.

Figure 1:
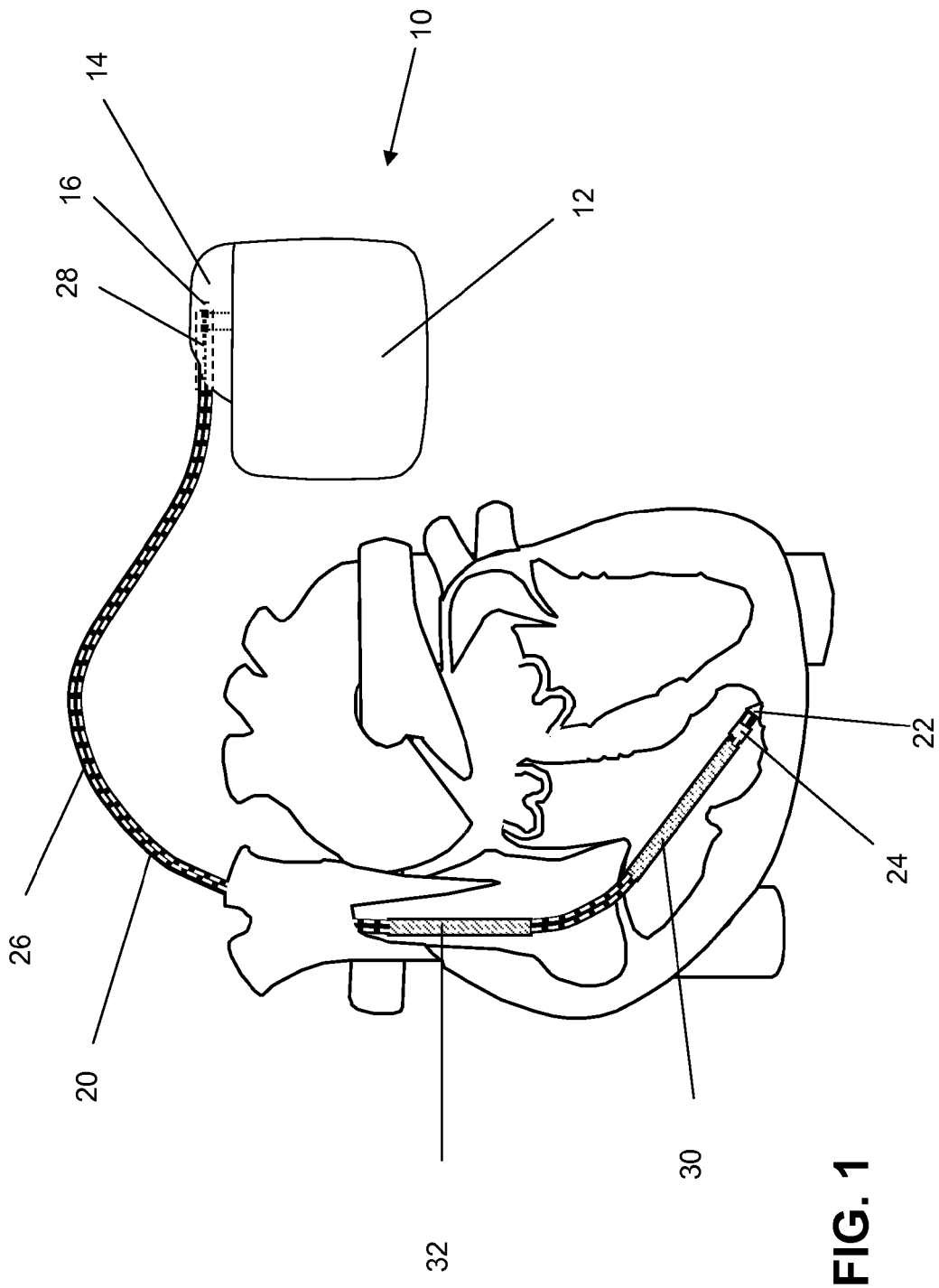
FIG. 1 shows an implantable heart stimulator and an implantable electrode lead connected thereto as the implantable medical device.

The electrode lead 20 also constitutes an implantable medical device in the sense of this invention. Electrode poles in the form of a point electrode or tip electrode 22 and a ring electrode 24 arranged nearby are arranged on the distal end of the electrode lead 20 in a known manner. The electrode poles 22 and 24 are designed so that they serve to sense electric potentials of the (myocardial) heart tissue depending on the function of the heart stimulator to which the electrode lead 20 is connected, or they are designed to deliver electrical signals, for example, for delivering stimulation pulses to the surrounding heart tissue. FIG. 1 shows how the electrode poles, i.e., the tip electrode 22 and the ring electrode 24, the electrode lead 20 in the application case, are situated at the apex of a right ventricle of a heart.

The tip electrode 22 and the ring electrode 24 are each electrically connected to a plug contact 28 on the proximal end of the electrode lead 20 via at least one electrical conductor 22 each. The plug contact 28 has electrical contacts, which correspond to the electrical contacts 16 of the contact busing in the terminal housing 14 of the implantable heart stimulator. The electrical conductors 26 in the electrode lead 20 may be designed as approximately elongated cable conductors or as helically coiled conductors. Such conductors, which electrically connect the functional electrode poles to electrical contacts of the plug contact on the proximal end of the electrode lead 20, are referred to in the context of this text as functional conductors because they transmit electrical signals, which are used therapeutically, from a plug contact to the respective electrode pole, or they transmit signals representing electrical potentials that are sensed from the respective electrode pole to the plug contact and thus serve the elementary function of the medical device.

The electrical conductors 26, which connect the electrode poles 22 and/or 24 to the electrical contacts of the plug 28 of the electrode lead 20, are surrounded by an insulating sheath over most of their length, so that an electrical contact with the tissue of the heart is achieved in a targeted manner via the electrode poles.

In addition to the electrode poles 22 and 24, which typically serve to stimulate the heart tissue (ventricular in this case), the electrode lead 20 also has two large-surface-area electrode poles 30 and 32, which serve as defibrillation electrodes and are formed by at least one helically coiled, uninsulated wire.

It should be pointed out that the invention is explained below as part of this exemplary embodiment on the basis of a right ventricular heart pacemaker and defibrillator. Essentially, however, an ablation electrode lead may also serve as the medical device in the sense of this invention. In the application case, this ablation electrode lead also extends into the patient's heart and is controlled by a device located outside of the patient and is connected to this device for this purpose.

Figure 2:
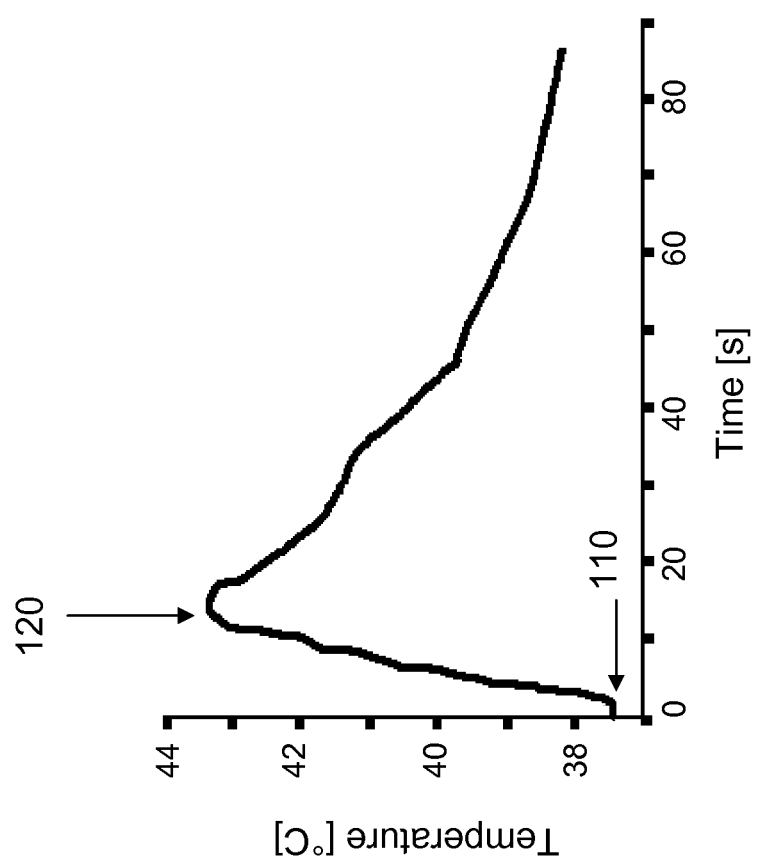
FIG. 2 shows an example of a temperature characteristic at the electrode tip.

FIG. 2 illustrates a typical temperature characteristic 100 of a conventional pacemaker/ICD electrode in an MRI machine. When the high-frequency alternating field is turned on in the MRI machine at time 110, the temperature rises rapidly, such that the steepness of the rise and the maximum achievable temperature depend greatly on the electrode position, based on the high-frequency alternating fields of the MRI. If the high-frequency alternating field is deactivated (at time 120), then the electrode tip cools again relatively rapidly due to its comparatively low thermal capacity.

FIGS. 3 to 8 show, in schematically simplified diagrams, two functional conductors each on the distal end of an electrode lead. The functional conductors are each identified as ZL1 (for the first electrode lead) and ZL2 (for the second electrode lead). The first lead ZL1 is connected as the electrode pole to a respective tip electrode 210, 310, 410, 510, 610 and/or 710, while the respective second functional conductor ZL2 is connected to a ring electrode 220, 320, 420, 520 and/or 720 as the electrode pole. Additional typical components of electrode leads such as an insulating sheath or terminal contacts on the respective proximal end have been omitted here for the sake of simplicity.

Figure 3A:
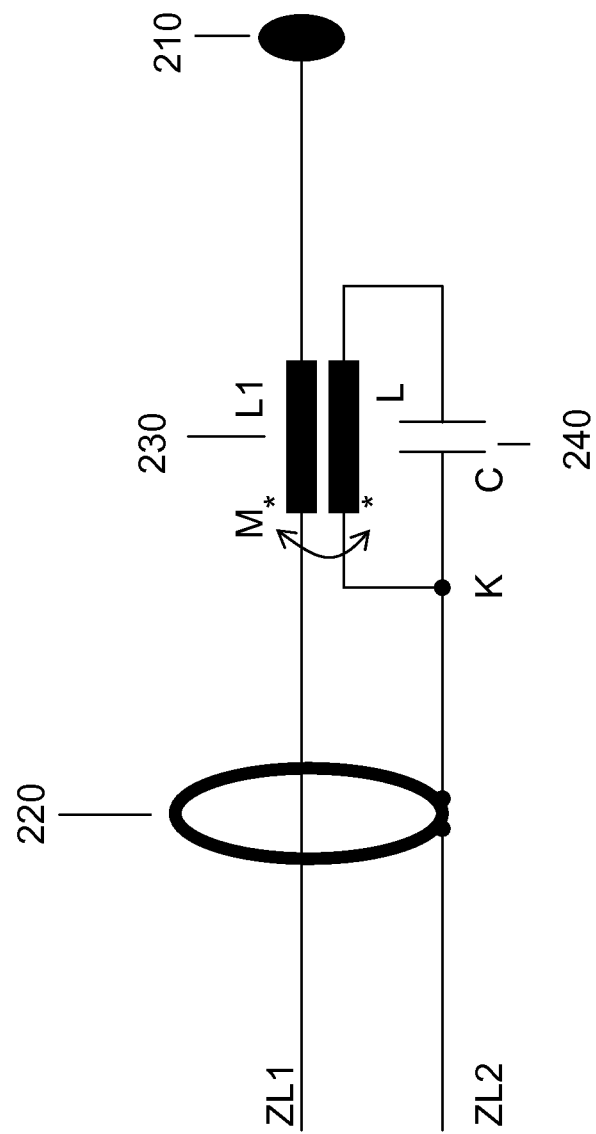
FIGS. 3A and 3B show examples of an MRI resonator suitable for inductive coupling of two functional conductors.

FIG. 3A shows the diverting lead according to the invention for the MRI-induced currents on the ring electrode 220 on the second functional conductor ZL2. The principle is to short-circuit the tip electrode 210 and ring electrode 220 with the oscillating circuit shown in the resonant case. To do so, a transformer 230 is connected between the first and second functional conductors ZL1 and ZL2. A capacitor 240, which is connected in parallel with the secondary winding L of the transformer 230, serves to tune the resonant frequency. This arrangement allows small component sizes, in particular coils having a very low inductance, and is thus easily compatible with the electrode design.

The resonant frequency is calculated according to the equation:

$$f_0 = \frac{1}{2\pi\sqrt{LC}}$$

Thus, at a capacitance C=1 pF, an inductance of "only" approximately 6.5 µH is required in the resonant circuit for a 1.5 T MRI. Such an arrangement may optionally be accommodated behind a ring electrode.

In another preferred implementation, C>10 pF is selected because otherwise the core-free implementation (because of saturation in the static magnetic field of the MRI) would require too many windings/a large geometry.

In the embodiment variant shown in FIG. 3A, the transformer is without a core. In another preferred implementation, a core is used, but only at field strengths greater than those of the anticipated MRI (for example, materials which become saturated only at approximately 1.7 T). Electrodes having a very effective core transformer may thus be constructed for use with 1 T and 1.5 T MRI machines.

The contact point K is provided on lead ZL2 in FIG. 3A as an example, that is, it is provided on the second functional conductor. The invention also relates to all implementation variants in which a contact point K on the first functional conductor ZL1 is contacted. In this case, the result is a series resonant circuit LC of the secondary winding L of the transformer 230 and of the capacitor 240.

Figure 3B:
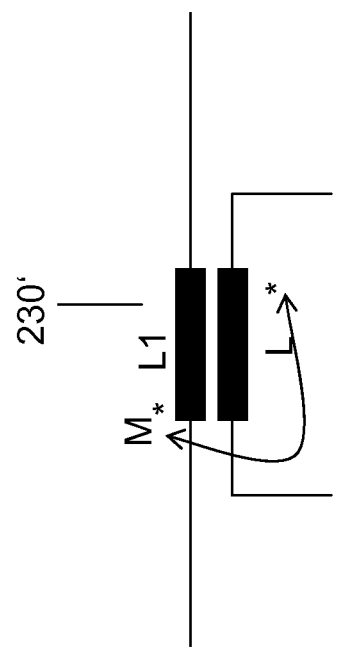

All the implementations are thus also the subject of the invention, when the transformer 230' is coupled in the reverse manner from that show in FIG. 3B.

Figure 4:
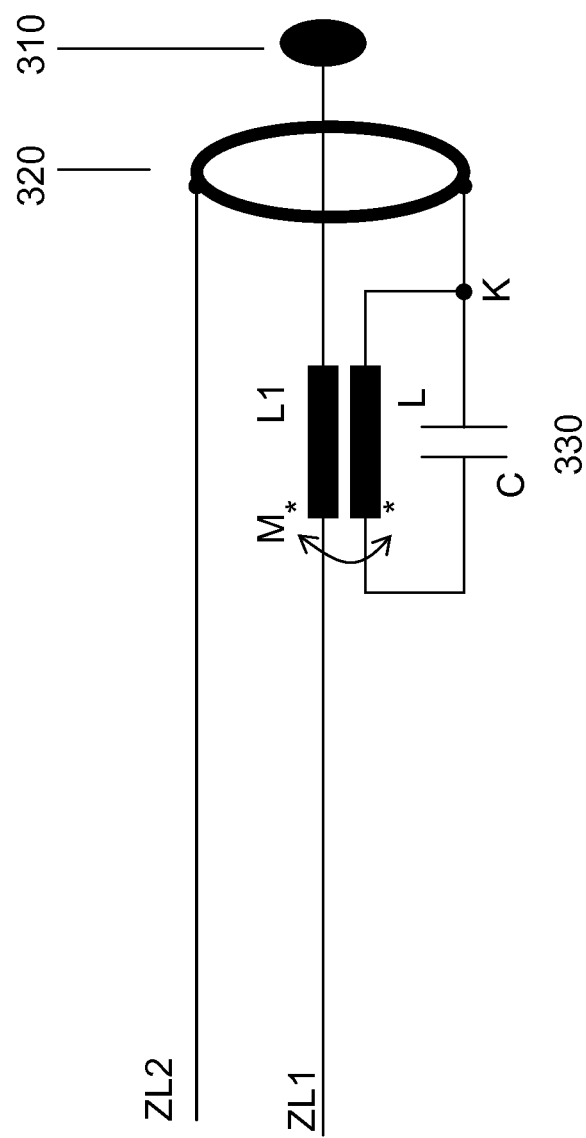
FIG. 4 shows an MRI resonator variant 2.

FIG. 3A shows the following:
210: tip electrode
220: ring electrode
230: transformer (with or without a core)
240: capacitor
ZL1: lead for tip electrode
ZL2: lead for ring electrode FIG. 4 shows an alternative embodiment, in which the resonator 330 with the transformer and the capacitor is attached proximally from the ring electrode 320. This embodiment offers the structural advantage that no reinforcement of the electrode is required in the area of the electrode tip.

Figure 5:
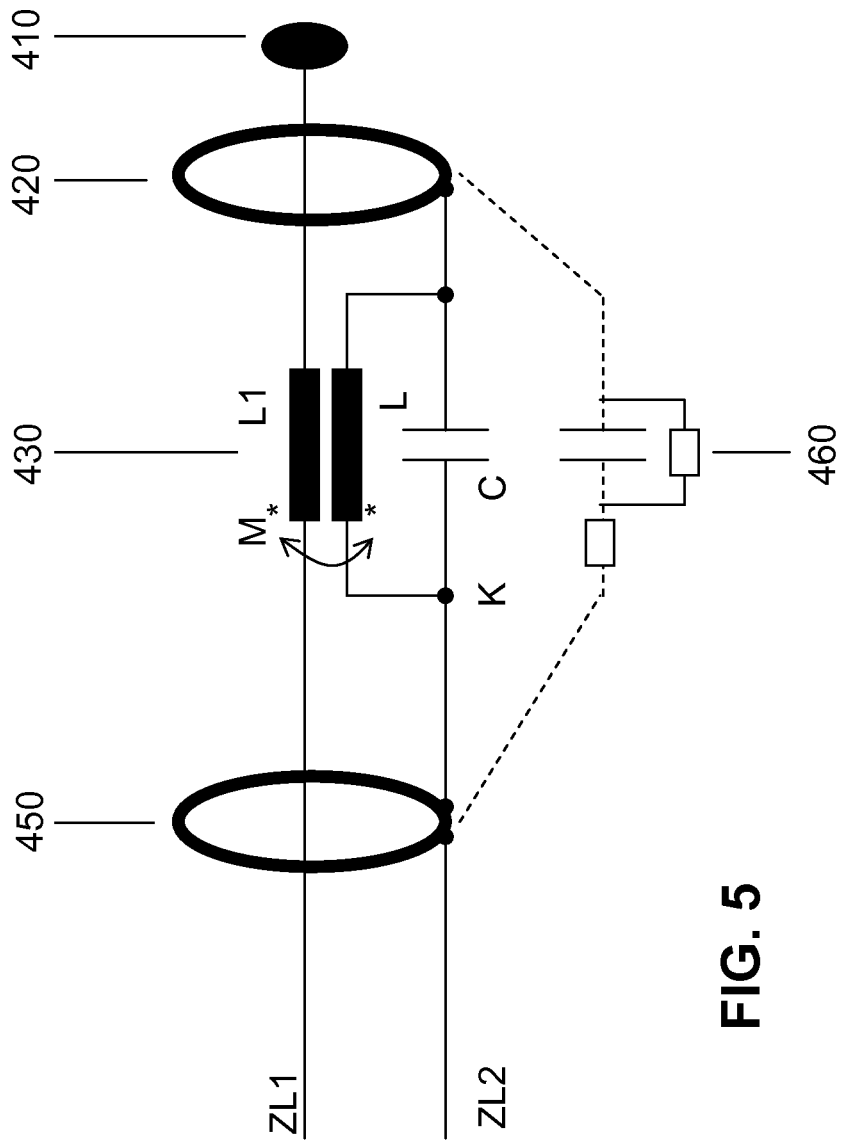
FIG. 5 shows an MRI resonator having two diverting leads.

FIG. 4 shows the following:
310: tip electrode
320: ring electrode
330: transformer and capacitor (resonator)
ZL1: lead for tip electrode
ZL2: lead for ring electrode FIG. 5 shows an expanded embodiment, in which an additional non-functional ring electrode 450, which is connected to the second functional conductor ZL2, is provided. The diverting lead of the MRI-induced RF energy is additionally diverted here to a non-functional ring electrode 450.

In this configuration, the parasitic body RC network 460 is taken into account and/or utilized in the dimensioning. The parasitic body RC network 460 is obtained in the use case—after implantation—from the electrical properties of the surrounding body fluids and the surrounding body tissue.

The advantage of this variant is the possibility of being able to divert higher energies and at the same time not having to optimize the dimensioning of the functional ring electrode 420 to the requirements of heat dissipation.

Figure 6:
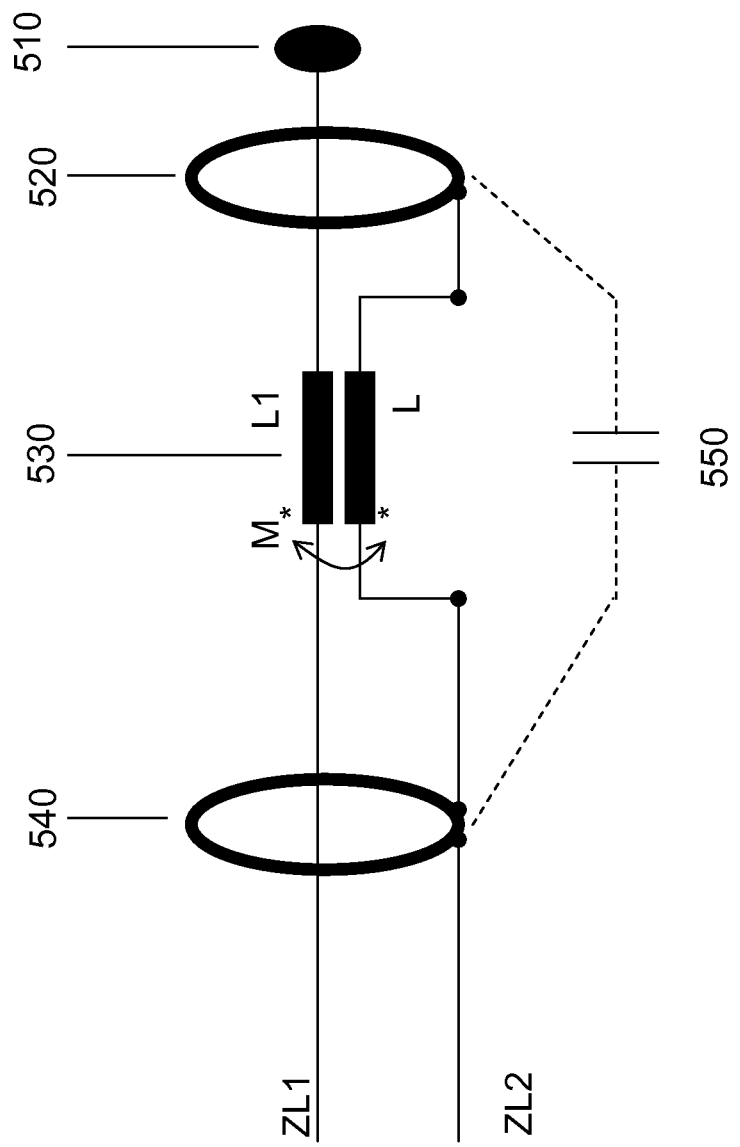
FIG. 6 shows an MRI resonator having two diverting leads in variant 2.

FIG. 5 shows the following:
410: tip electrode
420: functional ring electrode
430: transformer and capacitor (resonator)
450: additional ring electrode for dissipating heat
460: parasitic body network
ZL1: lead for tip electrode
ZL2: lead for ring electrode FIG. 6 shows a simplified embodiment in comparison with that in FIG. 5. This embodiment also has an additional non-functional second ring electrode 540 on the second functional conductor ZL2. The MRI-induced RF energy here is additionally diverted to the non-functional ring electrode 540.

However, the capacitor in the resonator circuit 530 is omitted in this configuration. The capacitance required for the resonance is replaced in the dimensioning by the parasitic body capacitance 550 to be expected in the use case.

Figure 7:
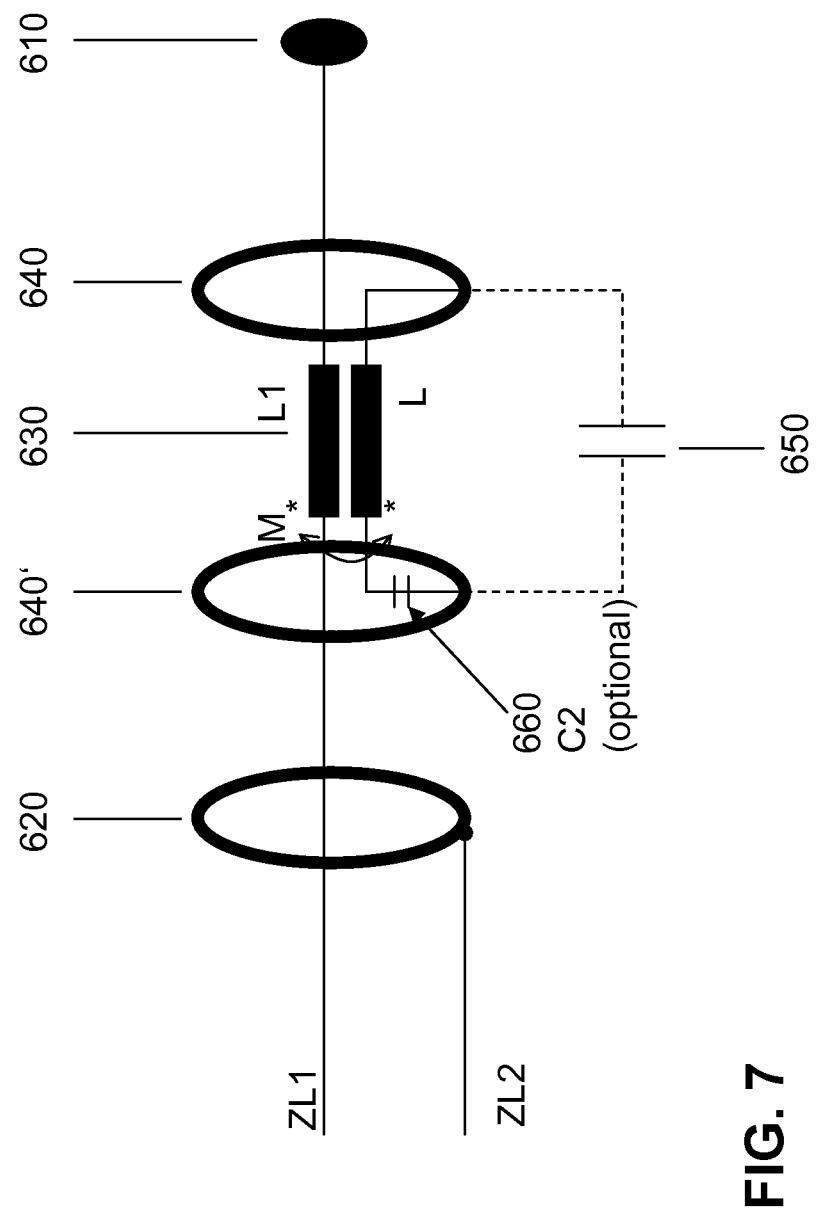
FIG. 7 shows an MRI resonator having multiple non-therapeutic rings for diverting energy.

FIG. 6 shows the following:
510: tip electrode
520: functional ring electrode
530: transformer
540: additional ring electrode for dissipating heat
550: parasitic body capacitance
ZL1: lead for tip electrode
ZL2: lead for ring electrode FIG. 7 shows an embodiment having several non-functional ring electrodes 640, 640' for dissipation of heat. The basic principle here corresponds to the embodiment variant according to FIG. 6 but offers the advantage that larger quantities of heat can be dissipated.

The functional ring electrode 620 is also not affected by the additional wiring. The embodiment variant according to FIG. 7 thus also makes do essentially without second functional conductors, so that the lead segments between the secondary winding LL of the transformer 530 and the respective ring electrode 640 and/or 640' act as the second functional conductor in the sense of this embodiment of the invention.

Figure 8:
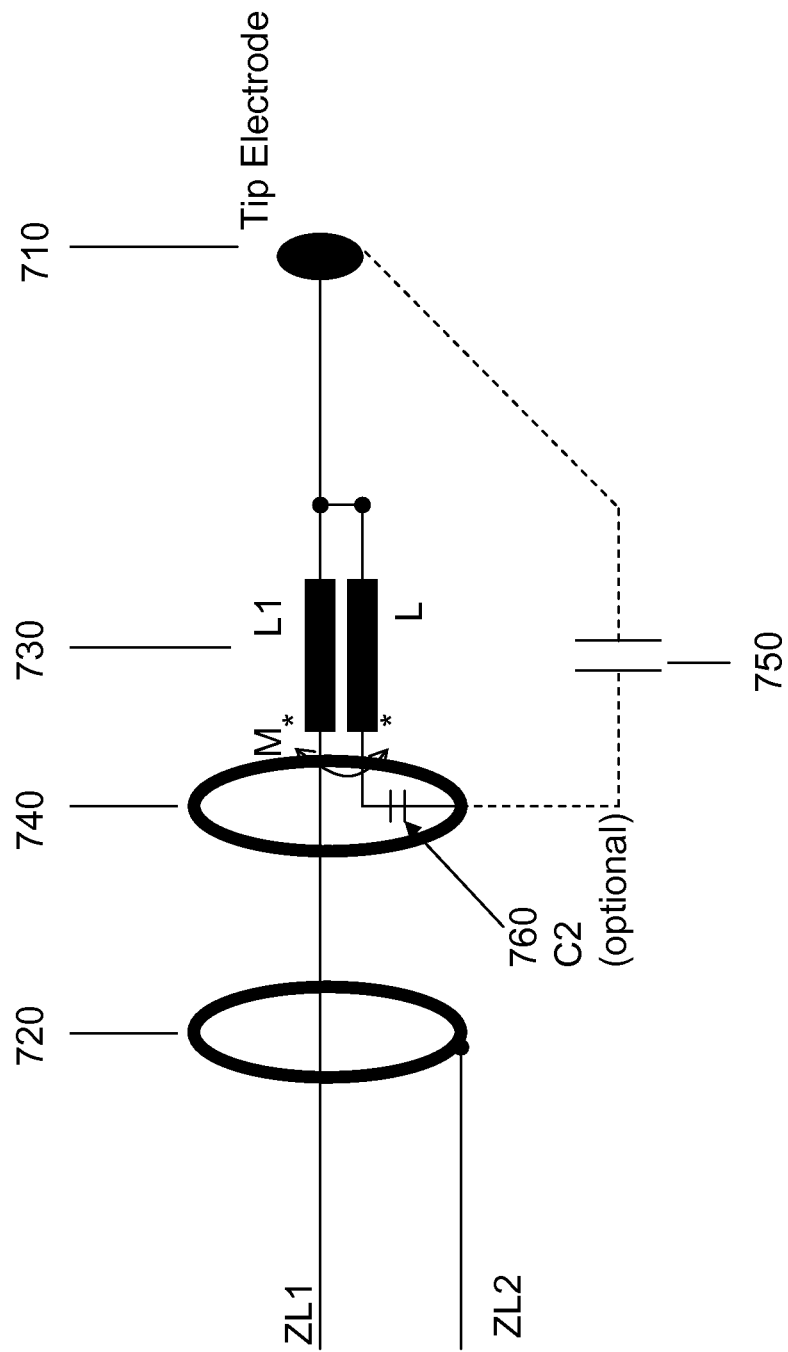
FIG. 8 shows an MRI resonator having a non-therapeutic ring electrode.

FIG. 7 shows the following:
610: tip electrode
620: functional ring electrode
630: transformer
640, 640': additional ring electrodes for dissipating heat
650: parasitic body capacitance
660: optional capacitor for adapting to the resonant case
Zl1: lead for tip electrode
Zl2: lead for ring electrode In the embodiment variant shown in FIG. 8, the principle of the embodiment variant according to FIG. 7 is simplified. The energy is dissipated here to a non-functional ring electrode 740. However, the functional ring electrode 720 is not influenced by the additional wiring.

FIG. 8 shows the following:
710: tip electrode
720: functional ring electrode
730: transformer
740: additional ring electrode for dissipating heat
750: parasitic body capacitance
760: optional capacitor for adapting to the resonant case
ZL1: lead for tip electrode
ZL2: lead for ring electrode It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:
1. An implantable medical device comprising:
at least one first functional conductor and at least one second functional conductor that are longitudinally extended electrical functional conductors configured to transmit therapeutic signals or diagnostic signals or both;

an electrode pole connected to the at least one second functional conductor, by which electrical current is delivered to surrounding bodily tissue, or with which electrical potentials in the surrounding bodily tissue can be sensed, or both, wherein the at least one first functional conductor and the at least one second functional conductor are inductively coupled at defined resonant frequencies, such that RF energy of the at least one first functional conductor is diverted to the at least one second functional conductor, and the RF energy is delivered, via the at least one second functional conductor and the electrode pole connected to the at least one second functional conductor, to the surrounding bodily tissue; and, a transformer connected between the at least one first functional conductor and the at least one second functional conductor, wherein said transformer is configured to couple the at least one first functional conductor and the at least one second functional conductor, wherein the transformer comprises a core of ferromagnetic core material, and, wherein the core of ferromagnetic core material comprises a saturation that begins only at a magnetic field strength higher than an MRI magnetic field strength applied by an MRI machine such that said saturation be ins at approximately 1.7 T.

2. The medical device according to claim 1, wherein the implantable medical device is a stimulation electrode lead.

3. The medical device according to claim 1, wherein the at least one second functional conductor is connected to the electrode pole via a ring or coil electrode.

4. The medical device according to claim 1, wherein the implantable medical device comprises a capacitor connected in parallel or in series with a winding of the transformer.

5. The medical device according to claim 4, wherein one or more of the transformer and the capacitor is tuned to a resonant frequency, such that a parasitic capacitance of the surrounding bodily tissue is taken into account in tuning.

6. The medical device according to claim 1, further comprising at least one ring electrode, wherein the at least one second functional conductor is electrically connected to the at least one ring electrode as another electrode pole configured specifically to divert the RF energy.

* * * * *